United States Patent

Jury

[11] Patent Number: 6,026,687
[45] Date of Patent: Feb. 22, 2000

[54] STRESS TESTING AND RELIEVING METHOD AND APPARATUS

[76] Inventor: Brent Felix Jury, Mahoetahi Road, RD 42, Waitara, New Zealand

[21] Appl. No.: 08/981,979

[22] PCT Filed: Jul. 15, 1996

[86] PCT No.: PCT/NZ96/00075

§ 371 Date: Jan. 9, 1998

§ 102(e) Date: Jan. 9, 1998

[87] PCT Pub. No.: WO97/04291

PCT Pub. Date: Feb. 6, 1997

[30] Foreign Application Priority Data

Jul. 14, 1995 [NZ] New Zealand ............................. 272581

[51] Int. Cl.[7] .............................. G01H 9/00; G01H 13/00
[52] U.S. Cl. ................................................. 73/582; 73/579
[58] Field of Search .............................. 73/579, 582, 583, 73/778

[56] References Cited

U.S. PATENT DOCUMENTS

| | | | |
|---|---|---|---|
| 2,729,972 | 1/1956 | Schidetzky et al. | |
| 3,622,404 | 11/1971 | Thompson | 73/579 |
| 3,816,927 | 6/1974 | Theurer et al. | |
| 4,122,723 | 10/1978 | Levizzari et al. | 73/579 |
| 4,381,673 | 5/1983 | Klauba et al. | 73/579 |
| 4,446,733 | 5/1984 | Okubo | |
| 4,823,599 | 4/1989 | Schneider | 73/579 |
| 5,085,080 | 2/1992 | Yu | |
| 5,195,046 | 3/1993 | Gerardi et al. | 73/583 |
| 5,242,512 | 9/1993 | Bagley et al. | |
| 5,520,052 | 5/1996 | Pechersky | |

FOREIGN PATENT DOCUMENTS

WO 91/19173  12/1991  WIPO.

*Primary Examiner*—Max Noori
*Attorney, Agent, or Firm*—Klauber & Jackson

[57] ABSTRACT

An apparatus for testing and stress relieving metal components comprising a vibration means (28), attachment means (30), control means (2) and measuring means (13,31), the attachment means (28) being configured and arranged to, in use, directly vibration couple the vibration means (28) to a metal component (40), the control means (2) controlling actuation of the vibration means (28), and the measuring means (13,31), in use, measuring the amplitude of vibration in the said metal component (29).

15 Claims, 3 Drawing Sheets

STRESS TESTING AND RELIEVING METHOD AND APPARATUS

TECHNICAL FIELD

This invention relates to apparatus for and a method of determining the resonance frequency of a metal component, and to using that information as a guide to the presence of stress in the metal component. The invention also relates to apparatus for and a method of relieving residual stress build up in a metal component.

BACKGROUND ART

All metal components suffer from a degree of residual stress build up caused by, for example, mechanical or thermal loading. This loading may be repetitive in nature such as is experienced, for example, by railway lines, valve springs and engine blocks, or may be a one time event, such as the thermal loading reulting during welding. The presence of stress affects the physical properties of a metal component and can result in stress fatigue and failure of the component.

Techniques for the relief of residual stress build up are known. Generally the known techniques involve heating the component to above its recrystalisation temperature, thereby allowing the crystalline structure to reformulate at a lower energy level. Such techniques are costly, and the process can take days to complete as a long cooling down period is usually required. This means a component will be out of commission for at least a few days and possibly weeks. For larger components the problem is particularly difficult to deal with, as the availability of a sufficiently large oven can be difficult to locate.

Methods available for measuring residual stress build up are not in widespread useage. Current practise is generally simply to subject a metal component to thermal stress relieving techniques regardless of the actual need. Therefore a significant wastage of resources arises in heat treating the those metal components not requiring stress relief.

A related problem arise with elongate components such as railway lines and pipelines. A railway track is generally laid in such a way as to be under a neutral load condition at a predetermined temperature. When the track is above the neutral temperature the railway line as a whole is placed under compression as the sections expand. At excessive levels this can result in the track buckling. At temperatures lower than the neutral temperature the track lengths exist in tension. At some point if the tensile forces are high enough, ie the temperature is low enough, the sections of track can snap.

Because of the outcome of the snapping of sections of track is not as much of a safety hazard as buckling of track the neutral temperature is typically set above the average summertime temperature. In New Zealand the neutral temperature is set at around 30 degrees celsius.

Railway lines undergo considerable thermal cycling. They are also subjected to significant mechanical loading as trains ride over the rails. This can result in plastic deformation of the rails, that is, the rails stretch. When that happens the neutral temperature of the rails drops, and thus the risk of track buckling on hot days increases. It is generally accepted that railway lines need to be reset, or restretched, ie re-laid under tension in order to reset the neutral temperature, every ten years or so to minimise the risk of buckling. It is, at present, a costly and time consuming exercise to uplift a railway line and relay it. Significant resources are wasted on restretching sections of track which do not require any stretching because until now a convenient a method of testing a line to determine whether it requires restretching has not been available.

It is an object of the present invention to provide a method of and an apparatus for testing a metal component which overcomes at least some of the abovementioned problems, or which at least provides the public with a useful choice.

It is a further object of the present invention to provide a method of and an apparatus for relieving the build up of residual stress in metal components which overcomes at least some of the abovementioned problems, or which at least provides the public with a useful choice.

SUMMARY OF THE INVENTION

According to a first aspect of the invention there is provided a method of testing to determine a resonance frequency in a metal component comprising the steps of:

a). attaching a vibration means to a said metal component to provide a substantially direct vibration couple between the vibration means and the said metal component; and b). actuating the vibration means through a predetermined range of vibration frequencies at a predetermined rate and at a constant input amplitude to locate and measure a resonance frequency of the said metal component.

According to a second aspect of the invention there is provided a method of stress relieving a metal component, the method comprising carrying out the method of testing to determine a resonance frequency, and then further comprising the steps of:

i). actuating the vibration means at above or below the measured resonance frequency for a predetermined period of time to relieve a degree of residual stress in the said metal component;

ii). repeating step b). of the method of the first aspect of the invention to obtain a second measurement of the said resonance frequency;

iii). comparing the first and second measurements of the said resonance frequency to provide an indication of the change in residual stress in the said metal component; and iv). repeating steps i), ii) and iii) until the change in the measured resonance frequency from one measurement to the next is at or below a predetermined level.

Preferably in step iii). the vibration means is actuated at a frequency below the first measured resonance frequency of the metal component.

Desirably the predetermined period of time in step i). of the second aspect of the invention is between 15 and 45 minutes.

According to a third aspect of the invention there is provided a method of stress relieving a metal component during and/or after welding the said metal component, the method comprising the steps of:

i). ensuring that the said metal component and any appendage to be welded to the said metal component vibrate as a single unit;

ii). carrying out the method according to the second aspect of the invention, during which welding on the said metal component can be performed.

According to a fourth aspect of the invention there is provided a method of testing a metal component to determine the need for stress relieving comprising the steps of:

i). obtaining a reference resonance frequency from a reference metal component having a known low stress level, using the method according to the first aspect of the inventon;

ii). determining the resonance frequency of the test metal component using the method according to the first aspect of the invnetion; and iii). comparing the resonance frequency of the reference metal component against the resonance frequency of the test metal component, and if the resonance frequency in the test metal component differs from that of the reference metal component stress relieving of the test metal component is required.

According to a fifth aspect of the invention there is provided a method of establishing a reference resonance frequency profile for a reference metal component at a known stress level at a particular temperature, the method comprising the steps of:

i) carrying out the method according to the first aspect of the invention on the reference metal component;

ii) measuring the temperature of the reference metal component; and iii) repeating steps i) and ii) at each of a range of temperatures of the reference metal component to obtain a resonance frequency at each temperature.

According to a sixth aspect of the invention there is provided a method of testing the stress level in a metal component, the method comprising the steps of:

i). carrying out the method according to the first aspect of the invention on the metal component to be tested at a specific temperature of the said metal component;

ii). repeating step i). at a range of different temperatures to establish a resonance frequency profile for the test metal component;

iv). comparing the resonance frequency profile of the test metal component with a reference resonance frequency profile for a reference metal component obtained according to the method of the fifth aspect of the invention.

Preferably in the method according to the sixth aspect of the invention the said test and reference metal components are sections of railway line in situ, and any significant difference in the resonance frequency profile of the test section of railway track from the resonance profile of the reference section of railway track indicates that the test section requires relaying.

Desirably in the method of the sixth aspect of the invention the resonance frequency profile of the test section of railway track is compared against a pair of reference resonance frequency profiles wherein the two reference sections of track are at the same stress level but at a different temperatures, such that if the resonance frequency profile of the test set of track lies between the two reference resonance profiles no relaying is indicated as required.

Preferably in the sixth aspect of the invention the two reference sections of track are at the same stress level at temperatures separated by six degrees celsius.

Preferably in the sixth aspect of the invention the vibration means is actuated through a range of vibration frequencies from 0 to 130 Hz.

Preferably in the sixth aspect of the invention the temperature measuring device is a pyrometer.

Preferably in the sixth aspect of the invention the range of temperatures at which the reference resonance frequencies are measured is from 0 to 35 degrees celsius.

According to a seventh aspect of the invention there is provided an apparatus comprising a vibration means, attachment means, control means and measuring means, the attachment means being configured and arranged to, in use, directly vibration couple the vibration means to a metal component, the control means controlling actuation of the vibration means, and the measuring means, in use, measuring the amplitude of vibration in the said metal component.

Desirably the apparatus further comprising temperature measurement means to, in use, measure the temperature of the said metal component.

Preferably the vibration means comprises a motor adapted to drive a shaft on which an eccentric weight is mounted. Advantagously the vibration control means includes a speed adjustment means to adjust the speed of the motor. Preferably the vibration control means further comprises a converter to convert a feedback speed signal measured from the shaft to a frequency signal and a speed control signal, the frequency signal being displayed by a frequency display means, and the speed control signal being adjusted by the speed adjustment means to, in use, vary the frequency of vibration being induced in the said metal component.

Preferably the apparatus further comprises a timer means to, in use, set the period of time during which the variable speed controller actuates the vibration means.

Preferably the vibration measuring means comprises a transducer for converting the measured amplitude of vibration in the metal component to an electrical vibration amplitude signal for display by a vibration amplitude signal display means.

Preferably the vibration amplitude signal and the vibration frequency signal are converted to respective equivalent digital signals and processed by a suitable software program run by a computer to display a plot of the amplitude of vibration over time against the frequency of vibration on a monitor and/or printer.

BRIEF DESCRIPTION OF THE DRAWINGS

Preferred embodiments of the invention will now be illustrated, by way of example only, with reference to the accompanying drawings in which.

DETAILED DESCRIPTION OF THE DRAWINGS

Figure 1:
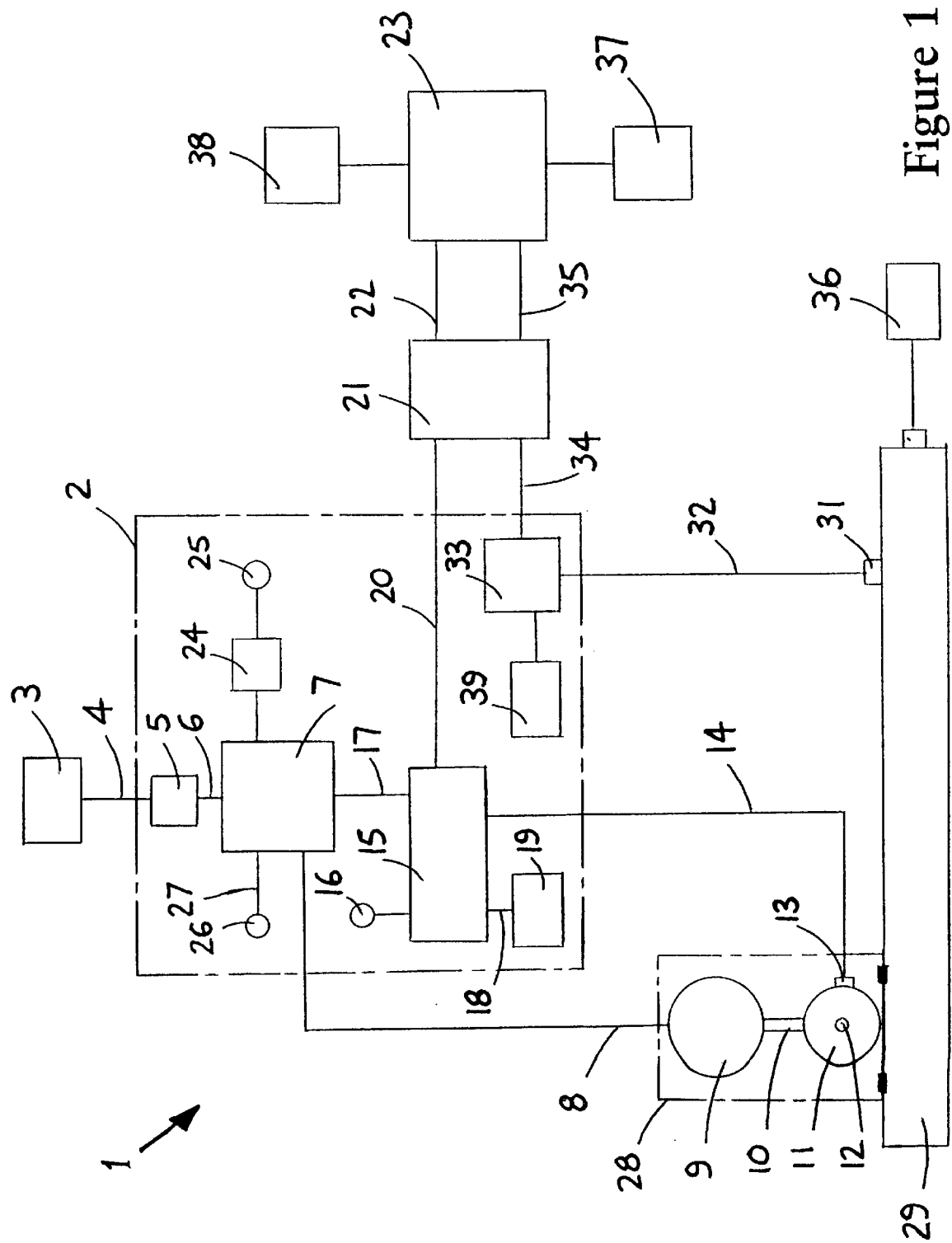
FIG. 1: illustrates an apparatus according to a preferred embodiment of the invention.

Referring to FIG. 1, an apparatus, as generally indicated at 1, according to a preferred embodiment of the invention, is illustrated.

The apparatus 1 comprises a vibration generator 1a, a control unit 2 to control the operation of the vibration generator 1a, clamps 30 to attach the apparatus 1 to a component to be tested or stress relieved, and a vibration transducer 31 to measure the amplitude of vibration induced in the component being tested or stress relieved.

The control unit 2 functions to control each step of the methods of the second aspect of the invention, and is central to the analogue signal processing circuits of the apparatus 1. The control unit 2 incorporates a power supply 3, which, for example, may be mains power supply at 230V AC, 50 Hz, connected through a cable 4 to a suitable three phase transformer 5 to transform the input power to a three phase power supply. The output three phase power 6 can be connected to a variable speed driver 7 to limit the amount of power being fed through a cable 8 to drive a motor 9 which forms part of the vibration generator 1a. The motor 9 can, for example, be a 750 W dual pole three phase motor.

Figure 2:
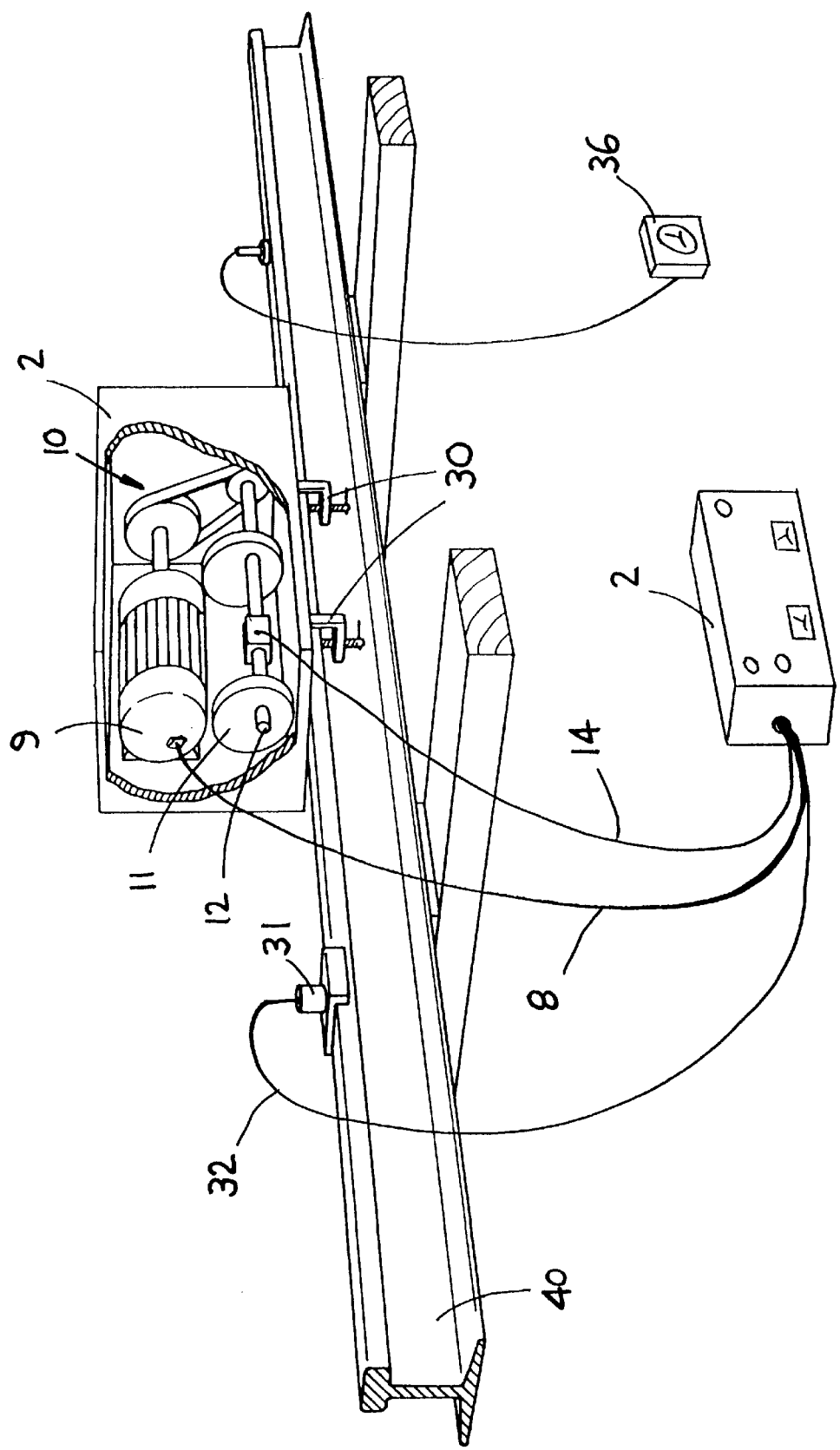
FIG. 2: illustrates the apparatus of FIG. 1 being used to test a section of railway line in accordance with the method of the invention.

The motor 9 is coupled via a coupling arrangement 10 to rotate eccentric weights 11 about a shaft 12. The coupling arrangement 10 is preferably two pulleys and a belt to couple the shaft of the motor 9 to the shaft 12 rotating the eccentric weights 11. The physical arrangement is seen in FIG. 2.

A shaft speed measuring device, preferably a tachometer 13, is mounted on the shaft 12. The output speed signal provides a feedback signal which is fed via line 14 to a speed signal processor 15. The speed signal processor 15 converts the signal to a variable speed control signal which is adjusted as required by a speed control knob 16 and sent via line 17 to the speed driver 7. Adjusting the speed knob 16 will increase or decrease the shaft speed of the motor 9 and hence control the frequency of vibration.

Figure 3:
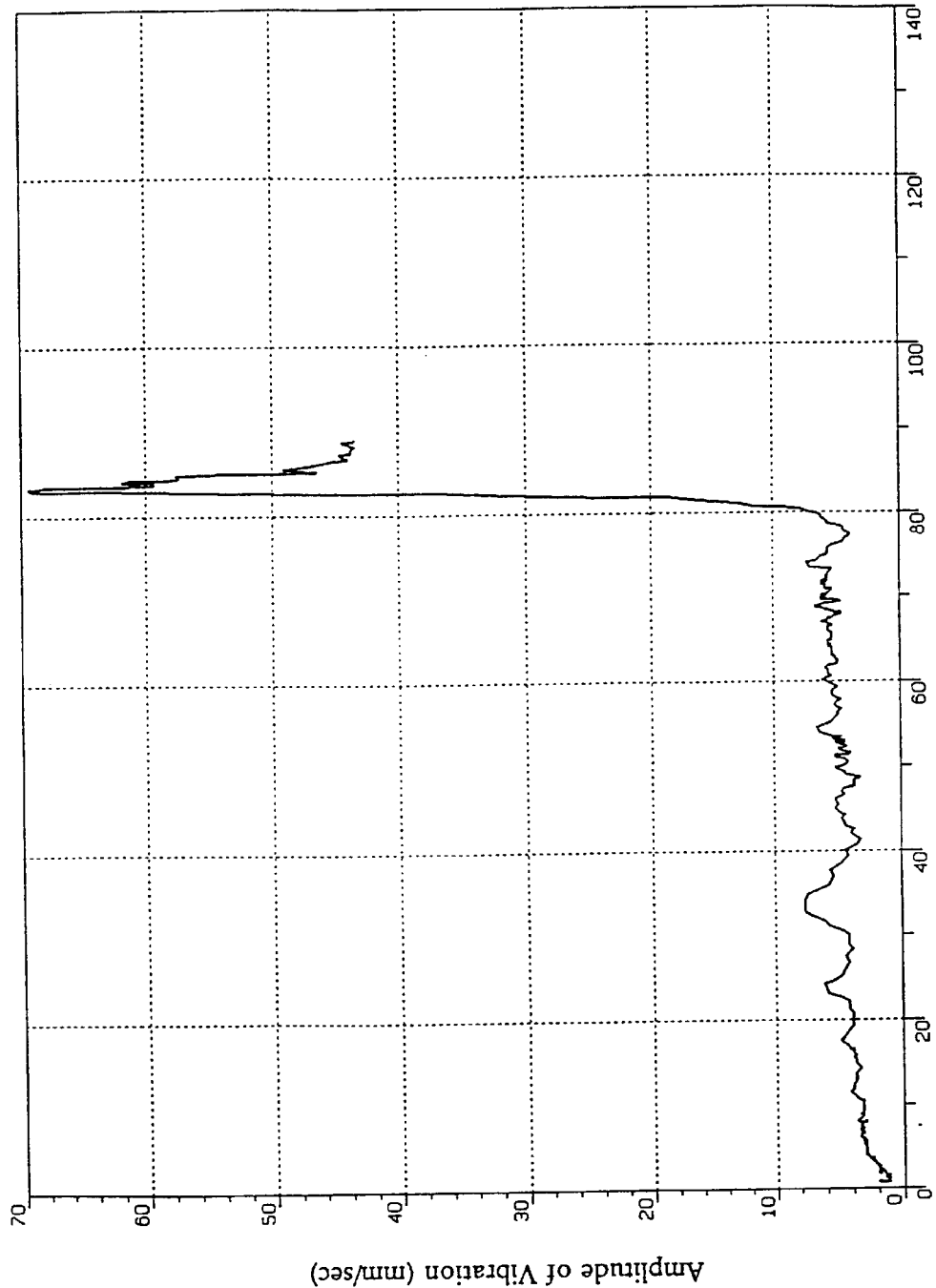
FIG. 3: illustrates a typical graph of frequency of vibration against amplitude of vibration for a metal component undergoing the method of testing demonstrated in FIG. 2.

The speed signal processor 15 also provides a frequency signal which is sent via line 18 to be displayed by a frequency meter 19. The frequency signal is also scaled by the processor 15 and the output frequency of vibration signal is sent via line 20 to an analogue to digital converter (ADC) 21. The output digital frequency of vibration signal is received by a computer 23 via line 22 to provide the X plot on a graph, an example of which is shown in FIG. 3.

A scanning circuit comprising a timer, run and scan ramp control components 24, and a selector switch 25 function to allow the eccentric weights 11 to rotate to within the operating frequency range desired. In the case of the method of testing railway lines, the preferred range of vibration frequencies is generally between 0 and 130 Hz. A protection feature in the form of a timer 26 connected via 27 to the speed driver 7 may be used to limit the time during which the testing or stress relieving methods operate to ensure the vibrations induced in a piece of metal are not vibrated for an undesirable period of time. The timer 26 desirably displays the count down time of an operation.

The eccentric weights 11 are adjustable about the shaft 12 to vary the input amplitude of the vibration. This input amplitude of vibration is adjustable so as to accommodate various test conditions. For example, the amplitude of vibration to test sections of railway line as described more with reference to FIG. 2 is generally between 4 to 12 mm/sec but more preferably is about 8 mm/sec. Generally, the lower the temperature recorded for a railway line, the higher the input amplitude of vibration in this range required to obtain workable data for comparison purposes.

The clamping means 30 attach and secure the vibration unit 28 to the metal component 29 so the weights 11 are adjacent the metal component 29 before any operation commences.

A suitable vibration transducer 31, preferably an inductive-type, is mounted by suitable mounting means on the metal 29, preferably at a predetermined distance from the vibration unit 28 to measure, in millimeters per second, the amplitude of vibration of the metal component 29 during use. The electrical transducer signals measured are fed via 32 to a vibration signal processor 33 for signal conditioning purposes. The measured amplitude of vibration is displayed on vibration meter 39. The vibration meter 39 measurements may in use be checked and calibrated by using an accelerometer (not shown) which is a precision instrument which is capable of accurately measuring the amplitude of vibration being induced in a piece of metal being vibrated by the vibration unit 28.

The output amplitude of vibration signals are also sent via 34 to the ADC 21 to be converted from analogue to digital signals representing the amplitude of vibration measured in the metal 29. The output digital signals 35 are fed to the computer 23 to provide the Y plot on a display graph as shown in FIG. 3.

A metal temperature measuring device, preferably a pyrometer 36, is connected to the metal 29 to measure and display the temperature of the metal 29.

The computer 23 is controlled by a spectrum analysing software program designed to process the incoming data received via lines 22 and 35 and to plot the results on a graph to indicate the integrity of the metalurgical structure in the metal 29. These graphs give an indication as to the dynamic changes occuring to the metalurgical structure at various stages when a piece of metal is being stress relieved, or offers an indication of the metalurgical structure when a piece of metal is simply being scanned or tested.

A computer printer 37 is desirably used with the computer 23 to print out the results of the testing and/or stress relieving being done at each stage of an operation if desired. A sample of a print out using the printer 37 is shown in FIG. 3. It is seen from the plotted graph of the amplitude of vibration over a frequency range that the amplitude of vibration remains fairly constant until the resonant frequency of the metal component is reached at about 80 Hz. At the frequency of vibration increases from 80 Hz to 85 Hz the amplitude of vibration is seen to escalate to a peak and then descend until the vibration unit shuts down at about 90 Hz. The resonant frequency level is noted for comparison purposes.

As a further monitoring feature, the processed data may be displayed on a computer monitor 38. This monitor 38 can be useful for monitoring aspects of the dynamic changes occuring in the metal.

Referring now to FIG. 1, the apparatus 1 is to be used to carry out the methods of testing and stress relieving a metal component according to further aspects of the invention, are described.

Vibrational stress relief can generally be conducted in under an hour and does not require a curing or cooling off period as is required in, for example, thermal stress relief techniques. Another advantage over thermal stress relief is that as a component may be stress relieved within a few hours the metal component need not be out of commission for days as normally occurs when thermal stress relief techniques are relied on.

For larger metal components such as a truck chassis, the vibration unit 28 of the apparatus 1 can be firmly clamped to the chassis in position. It is essential that a substantially direct couple between the vibration unit 28 and the truck chassis is made. An initial test or scan is done to establish where the resonant frequency of the chassis is by using the speed knob 16 to increase the speed and hence the frequency of the vibrations being induced in the chassis until the vibration meter 39 shows a spike being recorded indicating a marked increase in vibration amplitude. The frequency is noted on the frequency meter 19 and this frequency is the set frequency used during stress relieving.

The input vibration amplitude is set by adjusting the offset placement of two eccentric weights relative to each other about the shaft 12. The vibration level noted during the initial scan to find the resonant frequency is checked to ensure it is within the safe acceptable range of vibration to be used during stress relieving. If the vibration level needs adjusting the weights 11 are adjusted and the vibration level checked. The acceptable range is generally between 4 mm/sec and 12 mm/sec, and depends on the metal being used and the type of metal component.

The timer may be set to within the desired period of time for stress relieving which is generally under 40 minutes and is preferably about 25 minutes for most metal components. The switch 25 is triggered and the speed knob 16 adjusted to ramp up the frequency to the desired set frequency. The predetermined vibration level is checked also.

The vibration unit 28 is run, for example, for 25 minutes and then stopped. A printout in graph form may be made on the computer printer 37 before and after carrying out the stress relieving steps of the method to see the difference the operation has made to the section of chassis which has been stress relieved. The other sections of the chassis may then be stress relieved by repositioning the vibration unit 28 and repeating the method of stress relieving as detailed above.

The apparatus 1 of FIG. 1 may also be used to carry out a method of aiding the welding process and/or improving the results of a weld.

This method may be carried out during or after the welding process has taken place. This method includes attaching the vibration unit 28 to the metal component to be welded desirably by the clamp 30 and vibrating the metal component to establish the operating frequency level which is generally below the resonant frequency of the metal. This is generally between 85 and 110 Hz. The vibration amplitude is also checked.

The welding then commences while the apparatus 1 vibrates the metal component. The apparatus 1 continues to operate for about 30 minutes at the correct frequency and vibration amplitude, immediately after the welding has been completed.

As a result of the vibration treatment it has been found that the weld produced has an improved heat affected zone and the amount of distortion is minimised. For alloy cylinder heads machining work may be carried out alot sooner than would otherwise be possible.

It will be appreciated that smaller components may be clamped to a vibration table, the metal top of which is mounted on rubber pads, and the vibration unit 28 is mounted to the top also. The essential aspect of this variation is that the all three parts must be firmly secured together for direct coupling to ensure the vibrations are properly induced in the metal component to be tested and/or stress relieved.

The apparatus of the invention is particularly suited to the method of testing a section of railway line 40 in situ. This method is conducted to determine whether a section of line remains within predetermined safe operating parameters. It has been said that if sections of a railway line fall outside these parameters, adverse effects such as buckling or alignment problems may occur.

It is generally accepted that a metal elongates by an amount A which is proportional to both the temperature change dT and the length L of the rod. This can be represented by:

$$A = *(dT)L$$

where * is a constant characteristic of the material, called the coefficient of thermal expansion. The coefficient * represents a quantity per degree Celsius where the temperature change dT is expressed in degrees Celsius. Given this characteristic, it is seen that the rod will expand as the temperature increases and contract as the temperature decreases. This characteristic does not pose a problem when the rod functions as, for example, a beam, but if the ends of the rod are fixed between two supports, the supports will exert equal and opposite forces on the rod as the temperature increases, thus creating a state of stress in the rod. This stress will, over time, cause a dynamic change in the metalurgical structure of the rod.

One such situation where this occurs is with sections of railway line joined end to end. To deal with the stresses induced in the railway line caused by normal day to day temperature changes, sections of railway line should be laid to the same standard so that each section of line expands and contracts with changing temperatures so as not to induce an unacceptable level of stress in adjoining sections of line. An acceptable standard to which all sections of a line must be layed in New Zealand is to a neutral temperature of 30 degrees Celsius. At this temperature level the section of line is neither in tension or in compression. This is the reference standard against which all sections of line are measured against to determine whether a section of line tested is operating within acceptable operating parameters. The tolerance within which the acceptable operating parameter is a line which is at neutral temperature from between 27 to 33 degrees Celsius. If the line is outside this range the line requires relaying.

To achieve this desirable state, periodic uplifting and relaying of each section of railway line is done to ensure the integrity of the railway line is maintained. This uplifting and relaying is generally done every decade or so. However, this operation is costly and time consuming, and is a wsted effort if the line was in fact still functioning within acceptable operating parameters.

The apparatus according to an aspect of the invention is conveniently able to be used to carry out the method of testing the integrity of section of railway line in situ as follows.

As the stress levels within a section of railway line changes with temperature, a preliminary step with this method is to obtain reference data to be used as a "blueprint" or template representing the desirable operating parameters of a section of railway line. This is achieved by testing a section of line which has been layed to a standard which is acccepted as being within the safe operating parameters set by the railway industry. This blueprint is obtained by attaching the apparatus 1 to the industry standard section of line, and scanning the line at each degree of temperature and recording the results. The range of temperatures at which data is recorded for New Zealand conditions is generally between 0 degrees Celsius to 35 degrees Celsius. The range varies depending on the average temperatures which the line is subjected to in the country where the testing is taking place.

Each scan takes about 20 to 30 seconds to complete. The results show the amplitude or level of vibrations recorded on the line in millimeters per second and the frequency level at which these vibration levels are recorded. The results are desirably printed on a graph for ease of comparision purposes. The results are used during testing or scanning of railway lines as a "blueprint" or reference measure against which the results of each test is compared to determine whether a section of line tested has been functioning within the preset safe operating parameters or not.

The safe operating parameter of a section of railway line will vary depending on factors such as the atmospheric conditions with which a railway line has to function. It has been determined by testing using the apparatus 1 of the invention that a section of line at each degree of temperature change should be within a predetermined range of the desired resonance frequency.

The preferred steps of the method to test a section of railway line are as follows.

The vibrator unit 28 is clamped to a section of railway line 40 in situ by clamps 30. Preferably the vibrator unit 28 is clamped adjacent an end of the line 40 to be tested. The transducer 31 is mounted to the line 40 at a predetermined distance from the vibrator unit 28. This distance is preferably about 200 mm from the head of the weights 11. The weight setting is adjusted so as to get a reading of about 8 mm/sec at the frequency of about 105 Hz. This setting is used as the constant input vibration amplitude for all tests done on sections of railway line.

A temperature measuring device in the form of a pyrometer 36 is mounted on the line 40 to determine the temperature of the line 40 during scanning. The temperature recorded determines which blueprint of desired results is matched against the results of the search.

The scan timer 26 is set to complete the scan or test within a predetermined period of time. A scan generally takes about 20 to 30 seconds to complete. The scan switch 25 is activated and the control knob 16 adjusted to ramp the motor 9 up to a predetermined speed and thus to incrementally increase the vibrations induced in the line 40 to within a preset vibration frequency. The maximum vibration frequency is generally about 130 Hz, and the frequency range of interest is between 0 and 130 Hz for sections of railway line. The maximum frequency for scanning or testing purposes should desirably be slightly above a resonance frequency of the metal, but when stress relieving it should be slightly below the resonance frequency. If the vibrations being induced are at the resonant frequency of the railway track or line, a build up of the amplitude of vibration is induced and damage is likely to occur to the track and to the apparatus 1.

As the line is being scanned a user checks the monitor 38 to ensure the desired vibration amplitude is being induced in the line 40. Adjustments may be made during the scan by adjusting the speed knob 16 and noting the frequency level on the frequency meter 19.

The transducer 31 measures the actual vibration amplitude in the line 40 and provides a vibration amplitude signal to the computer 23. The measurements of amplitude in millimeters per second are monitored and displayed by the meter 39, and can be seen on the computer monitor 38 if desired. The tachometer 13 measures the speed of the shaft 12 which is converted to a frequency signal by processor 15 and is received by the computer 23 also. Both signals are processed by the software program to display the results on a graph. The results of any measurements may be printed by printer 37 or merely displayed on the monitor 38 or both.

The results of the test are then compared with the blueprint standard expected at the temperature measured by the pyrometer 36. If it is seen that the peak amplitude of the vibration signal, expected at between about 100 to 110 Hz, is less than the predetermined minimum standard vibration signal on the blueprint, then the line 40 is seen as being in tension. If the peak vibration signal is greater than the predetermined maximum standard vibration signal on the blueprint, the line 40 is seen as being in compression. Either result will mean the line 40 is not functioning within the desired operating parameters and should be uplifted from the railway line and relayed. If the result is that the peak vibration signal at the measured frequency level is within the predetermined range of acceptable standard vibration levels, then the section of line tested is seen to have met the industry standard and that section of railway line does not need to be uplifted from the line.

This method of testing offers a quick and convenient way of testing sections of railway line in situ without taking the costly and time consuming step of uplifting the line.

Wherein the foregoing reference has been made to integers or components having known equivalents, then such equivalents are herein incorporated as if individually set forth.

Accordingly, it will be appreciated that changes may be made to the above described embodiments of the invention without departing from the principles taught herein.

Additional advantages of the present invention will become apparent for those skilled in the art after considering the principles in particular form as discussed and illustrated. Thus, it will be understood that the invention is not limited to the particular embodiments described or illustrated, but is intended to cover all alterations or modifications which are within the scope of the appended claims.

I claim:

1. A method of stress relieving a metal component in situ, the method comprising the steps of:
   a. providing said metal component in situ, arranged and configured with adjoining components and attaching a vibration means to a said metal component to provide a substantially direct vibration couple between the vibration means and the said metal component;
   b. actuating the vibration means through a predetermined range of vibration frequencies at a predetermined rate and at a constant input amplitude to locate and measure a resonance frequency of the said metal component;
   c. actuating the vibration means at above or below the measured resonance frequency for a predetermined period of time to relieve a degree of residual stress in the said metal component;
   d. repeating step b. to obtain a second measurement of the said resonance frequency;
   e. comparing the first and second measurements of the said resonance frequency to provide an indication of the change in residual stress in the said metal component; and
   f. repeating steps c., d. and e. until the change in the measured resonance frequency from one measurement to the next is at or below a predetermined level.

2. The method of claim 1 wherein in step e. the vibration means is actuated at a frequency below the first measured resonance frequency of the metal component.

3. The method of claim 1 or claim 2 wherein the predetermined period of time in step c. is between 15 and 45 minutes.

4. A method of establishing a reference resonance frequency profile for a reference metal component at a known stress level at a particular temperature according to claim 1, the method comprising the steps of:
   i) carrying out steps a. and b. of the method of claim 1 on the reference metal component;
   ii) measuring the temperature of the reference metal component; and
   iii) repeating steps i) and ii) at each of a range of temperatures of the reference metal component to obtain a resonance frequency at each temperature.

5. A method of testing the stress level in a metal component in situ, the metal component being arranged and configured with adjoining components according to claim 4, the method comprising the steps of:
   i). carrying out steps a. and b. of the method of claim 1 on the metal component to be tested being at a specific temperature of the said metal component;
   ii). repeating step i). at a range of different temperatures to establish a resonance frequency profile for the test metal component; and iii). comparing the resonance frequency profile of the test metal component with a reference resonance frequency profile for a reference metal component obtained according to the method of claim 4.

6. The method according to claim 5 wherein the said test metal component is a section of railway line in situ and the reference metal component is a section of railway line, and any significant difference in the resonance frequency profile of the test section of railway line from the resonance profile of the reference section of railway line indicates that the test section of railway line requires relaying.

7. The method of claim 6 wherein the resonance frequency profile of the test section of railway line is compared against a pair of reference resonance frequency profiles, wherein the two reference sections of line are at the same stress level but at a different temperatures, such that if the resonance frequency profile of the test set of line lies between the two reference resonance profiles no relaying is indicated as required.

8. The method of claim 7 wherein the two reference sections of line are at the same stress level at temperatures separated by six degrees Celsius.

9. The method according to any one of claims 6 to 8 wherein the vibration means is actuated through a range of vibration frequencies from 0 to 130 Hz.

10. The method according to any one of claims 6 to 8 wherein the temperature measuring device is a pyrometer.

11. The method according to any one of claims 6 to 8 wherein the range of temperatures at which the reference resonance frequencies are measured is from 0 to 60 degrees Celsius.

12. An apparatus for stress relieving of a metal component in situ, the metal component being arranged and configured with adjoining components, the apparatus comprising:

a vibration means, attachment means, control means, vibration measuring means and temperature measurement means, the attachment means being configured and arranged to, in use, directly vibration couple the vibration means to a said metal component, the control means controlling actuation of the vibration means, the vibration measuring means and the measurement means, in use, measuring the amplitude of vibration and the temperature respectively in the said metal component;

wherein the metal component is a section of railway line and wherein the vibration means comprises a motor adapted to drive a shaft on which an eccentric weight is mounted;

wherein the vibration control means includes a speed adjustment means to adjust the speed of the motor; and wherein the vibration control means further comprises a converter to convert a feedback speed signal measured from the shaft to a frequency signal and a speed control signal, the frequency signal being displayed by a frequency display means, and the speed control signal being adjusted by the speed adjustment means to, in use, vary the frequency of vibration being induced in the said metal component.

13. The apparatus according to claim 12 further comprising a timer means to, in use, set the period of time during which the variable speed controller actuates the vibration means.

14. The apparatus according to claim 13 wherein the vibration measuring means comprises a transducer for converting the measured amplitude of vibration in the metal component to an electrical vibration amplitude signal for display by a vibration amplitude signal display means.

15. The apparatus according to claim 14 wherein the vibration amplitude signal and the vibration frequency signal are converted to respective equivalent digital signals and processed by a suitable software program run by a computer to display a plot of the amplitude of vibration over time against the frequency of vibration on a monitor and/or printer.

* * * * *